United States Patent [19]

Ginter et al.

[11] Patent Number: 4,481,167

[45] Date of Patent: Nov. 6, 1984

[54] SANITIZING COMPLEXES OF POLYOXAZOLINES OR POLYOXAZINES AND POLYHALIDE ANIONS

[75] Inventors: Sally P. Ginter, Sanford; Percy J. Hamlin, Midland, both of Mich.

[73] Assignee: The Dow Chemical Company, Midland, Mich.

[21] Appl. No.: 279,416

[22] Filed: Jul. 1, 1981

Related U.S. Application Data

[63] Continuation of Ser. No. 139,306, Apr. 11, 1980, abandoned, which is a continuation-in-part of Ser. No. 030,396, Apr. 16, 1979, abandoned.

[51] Int. Cl.$^3$ .................. A61K 31/74; C08G 73/00
[52] U.S. Cl. ..................... 422/29; 524/612; 424/78; 525/410
[58] Field of Search .............. 260/29.2 N; 524/612; 525/410; 422/29, 37; 424/78

[56] References Cited

U.S. PATENT DOCUMENTS

| | | | |
|---|---|---|---|
| 2,739,922 | 3/1956 | Shelanski | 424/80 |
| 2,826,532 | 3/1958 | Hosmer | 424/80 |
| 2,900,305 | 8/1959 | Siggia | 424/80 |
| 3,028,300 | 4/1962 | Cantor | 424/80 |
| 3,462,363 | 8/1969 | Mills | 210/37 |
| 3,898,326 | 8/1975 | Cantor et al. | 424/150 |
| 3,958,026 | 5/1976 | Leone et al. | 426/332 |
| 4,011,376 | 3/1977 | Tomalia et al. | 526/11.1 |
| 4,017,407 | 4/1977 | Cantor et al. | 424/80 |
| 4,113,857 | 9/1978 | Shetty | 424/80 |
| 4,144,211 | 3/1979 | Chamberlin et al. | 525/410 |

FOREIGN PATENT DOCUMENTS

1218466  1/1971  United Kingdom.

OTHER PUBLICATIONS

Schmidt et al., "Detergent/Iodine Systems", Soap and Chemical Specialties, 8/67.
Block "Disinfection—", 2nd Ed., 1977, Chap. 11, pp. 196–
Tomono et al., J. Poly. Sci., vol. 12, pp. 167–181, (1974).

*Primary Examiner*—John C. Bleutge
*Assistant Examiner*—A. H. Koeckert
*Attorney, Agent, or Firm*—Charles J. Enright

[57] ABSTRACT

The title complexes comprise (a) a poly-2-oxazoline or poly-2-oxazine, such as the homopolymers of polymerized 2-ethyl-2-oxazoline or 2-ethyl-2-oxazine, and (b) IBrCl$^-$ or polyhalide anion of the formula $(XY_{2n})^-$ where X and Y are individually chloride, bromide or iodide, but not both chloride, and n is 1, 2 or 3, and an independently supplied cation selected from the group consisting of alkali metals, alkaline earth metals, hydrogen and mixtures thereof. These complexes are readily prepared in either an aqueous or anhydrous environment at room temperature and are significantly more stable than either complexes of polyoxazolines or polyoxazines and halogen or interhalogen; or complexes of polyvinylpyrrolidone and polyhalide anions.

21 Claims, No Drawings

SANITIZING COMPLEXES OF POLYOXAZOLINES OR POLYOXAZINES AND POLYHALIDE ANIONS

CROSS-REFERENCE TO RELATED APPLICATIONS

This is a continuation of application Ser. No. 139,306, filed Apr. 11, 1980 now abandoned; which is a continuation-in-part of application Ser. No. 030,396, filed Apr. 16, 1979 and now abandoned.

BACKGROUND OF THE INVENTION

1. Field of the Invention

This invention relates to halophors. In one aspect, the invention relates to a novel class of complexes of 2-oxazoline or 2-oxazine polymers, polyhalide anions and independently supplied cations while in another aspect, the invention relates to the use of these complexes as sanitizing agents.

2. Description of the Prior Art

Halophors have long been known and the art is replete with various classes of such, processes for their manufacture, and a myriad of their alleged utilities. See, for example, *Disinfection, Sterilization and Preservation*, 2nd Edition, Chapter 11, Lea & Febiger (Philadelphia 1977) by S. S. Block. Of the many known halophors, probably the most common are those prepared from iodine ($I_2$) and polyvinylpyrrolidone. These materials are generally complexes of indefinite composition and are generally soluble in water. When solubilized, these complexes slowly liberate free iodine which is the active ingredient. These complexes can contain up to about 25 weight percent iodine although not all is available (titratable with $AgNO_3$) due to some being organically bound to the polymer. Many patents have issued regarding these complexes and U.S. Pat. Nos. 4,017,407; 3,898,326; 3,028,300; 2,900,305; 2,826,532 and 2,739,922 are exemplary.

Halophors or complexes of polyoxazolines or polyoxazines and halogens, interhalogens or pseudo-halogens, are described in U.S. Pat. No. 4,144,211 by Chamberlin and Bangs. These complexes represent a class of halophors distinct from the complexes of polyvinylpyrrolidone and have demonstrated utility as sanitizing agents. However, like complexes of polyvinylpyrrolidone, the total weight percent of iodine that these materials can complex is not entirely satisfactory.

SUMMARY OF THE INVENTION

According to this invention, water-soluble complexes useful as sanitizing agents comprise (a) a poly-2-oxazoline or poly-2-oxazine; (b) a polyhalide anion of the formula $(XY_{2n})^-$ where X and Y are individually chloride, bromide or iodide, but not both chloride, and n is 1, 2 or 3; and an independently supplied cation selected from the group consisting of alkali metals, alkaline earth metals, hydrogen and mixtures thereof. These materials are readily prepared at room temperature in either an aqueous or anhydrous environment and are significantly more stable than complexes of either poly-2-oxazoline or poly-2-oxazine and halogen, interhalogen or pseudo-halogen or complexes of polyvinylpyrrolidone and polyhalides. For example, not only can the complexes of this invention be prepared with a significantly greater $I_2$:polymer ratio than can analogous polyvinylpyrrolidone complexes at equivalent percent solid levels, but the instant complexes have a significantly lower viscosity than do analogous polyvinylpyrrolidone complexes at equivalent iodine loadings. This latter distinction is particularly significant because it permits the preparation of concentrated, aqueous, polymer-polyhalide complex solutions previously not obtainable with prior art complexes, notably polyvinylpyrrolidone-polyhalide complexes.

DETAILED DESCRIPTION OF THE INVENTION

The poly-2-oxazolines and poly-2-oxazines here used are known compounds consisting essentially of m units (I), randomly joined, and are readily prepared by the ring-opening polymerization of substituted oxazolines or oxazines (III); followed optionally by hydrolysis (II).

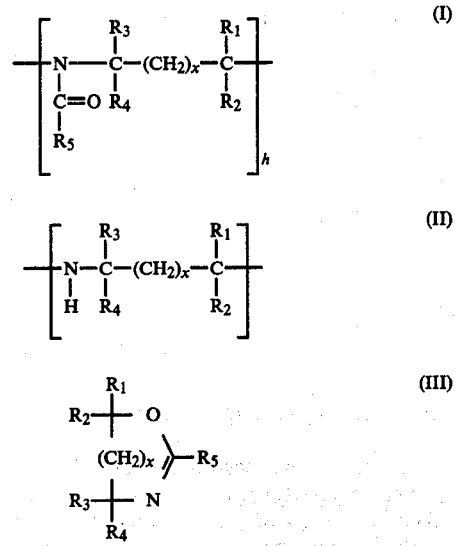

The substituents and subscript are later defined. The ring-opening polymerization is generally conducted in the presence of a cationic polymerization catalyst at a reaction temperature of about 0°–200° C. Typical catalysts include strong mineral acids, organic sulfonic acids and their esters, acidic salts such as ammonium sulfate, Lewis acids such as aluminum trichloride, stannous tetrachloride, boron trifluoride, and organic diazonium-fluoroborates dialkyl sulfates, and other like catalysts. This ring-opening polymerization is further described by Tomalia et., *Journal of Polymer Science*, 4, 2253 (1966); Bassiri et al., *Polymer Letters*, 5, 871 (1967); and Seeliger, German Pat. No. 1,206,585.

The polymers thereby obtained are linear, poly-2-oxazolines or poly-2-oxazines having a molecular structure consisting essentially of m repeating units (I). The polymers are easily deacylated by acid or base hydrolysis but since hydrolysis (deacylation) is generally best controlled under acidic conditions, acid hydrolysis is preferred. The partially deacylated poly-2-oxazolines or poly-2-oxazines thus have a molecular structure consisting essentially of m randomly joined units (I) and (II), illustratively depicted as

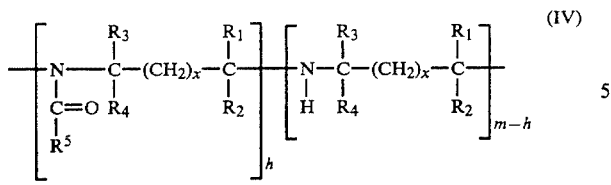

wherein: m is the total number of units; h is the number of acylated units; and m−h is the number of deacylated units.

"Poly-2-oxazolines" and "poly-2-oxazines" here include both the fully acylated and partially deacylated polymers. Partially deacylated polymers have at least one acyl group ($R_5C=O$) per polymer chain, i.e. h is at least one. Preferably, the polymers here used are no more than about 50 percent deacylated (h is at least about 50 percent of m) and most preferably no more than about 25 percent deacylated (h is at least about 75 percent of m). Fully acylated or nondeacylated polymers (h is or is about 100 percent of m) are most preferred.

As regards the substituents and subscript in the above formulae, $R_1$–$R_4$ are typically hydrogen or $C_1$–$C_3$ alkyl, $R_5$ is typically hydrogen or alkyl having up to about 18 carbon atoms, preferably a $C_1$–$C_4$ alkyl, phenyl or an inertly-substituted alkyl or phenyl, and x is 0 (an oxazoline) or 1 (an oxazine). By such terms as "inertly-substituted" is meant that the substituent does not substantially interfere with the ability of the polymer to complex a polyhalide anion. Illustrative inert substituents include halogen, ether oxygen, carbonyl, ester, etc. Exemplary $R_1$–$R_4$ substituents include hydrogen, methyl, ethyl and propyl and exemplary $R_5$ substituents include methyl, ethyl, propyl, pentyl, cyclohexyl, dodecyl, octadecyl, phenyl and their various halogenated, etherified, etc. derivatives.

Any member of the known classes of poly-2-oxazolines and poly-2-oxazines can here be used. Examples of suitable monomers from which the polymers (the term as here used includes copolymers) can be prepared include 2-H-2-oxazoline, 2-methyl-2-oxazoline, 2-ethyl-2-oxazoline, 2-propyl-2-oxazoline, 2-phenyl-2-oxazoline, 2-ethyl-4-methyl-2-oxazoline, 2-ethyl-5-methyl-2-oxazoline, 2-ethyl-5-dimethyl-2-oxazoline, 2-H-2-oxazine, 2-methyl-2-oxazine, 2-ethyl-2-oxazine, and the like, and combinations thereof. Poly-2-oxazolines (x is 0) are preferred to the poly-2-oxazines (x is 1) and poly-2-oxazolines wherein $R_1$–$R_4$ are hydrogen and $R_5$ is an alkyl radical of 1–4 carbon atoms are more preferred. Homopolymers prepared from either 2-ethyl-2-oxazoline (V) or 2-methyl-2-oxazoline (VI) are especially preferred.

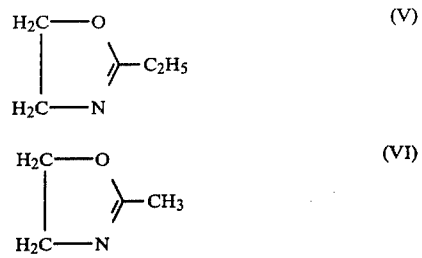

Polymers of particular interest, useful for preparing the complexes of this invention, are functionalized polymers, i.e. polymers prepared from a hydrophobe-initiated, ring-opening polymerization of 2-oxazoline and/or 2-oxazine monomers. These functionalized polymers are characterized by the presence of a hydrophobe radical attached to either or both (typically just one) terminal mer units of the polymer and can be illustratively depicted as

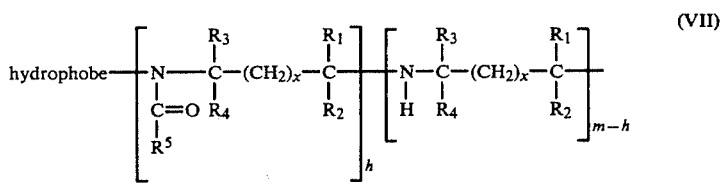

where the substituents and subscripts are as previously defined. Any organic compound that can initiate a ring-opening polymerization of 2-oxazoline and/or 2-oxazine monomer and which imparts detectable hydrophobic character to the resulting polymer can become the hydrophobe of the functionalized polymer. Typical of such compounds are the sulfonyl halides of long chain hydrocarbons, such as $C_8$–$C_{40}$ alkyls, aralkyls, etc.; esters of organic acids; $C_8$–$C_{40}$ alkyl halides; diphenyl ether sulfonyl halides; and the like. Polyisobutylene and dodecylbenzene sulfonyl chloride are illustrative. The functionalized polymers exhibit desirable surfactant properties and when complexed with polyhalide anions, provide a most unique sanitizing agent.

The nonfunctionalized polymers of this invention typically have a weight average molecular weight of at least about 10,000 as determined by gel permeation chromatography. More typically, these compounds have an average minimum molecular weight of about 20,000 and preferably of about 100,000. Practical considerations, such as preparation, handling, and the like are the only limitations upon the average maximum molecular weight of these polymers, although convenience prefers a maximum of about 800,000 and more preferably, of about 500,000.

The functionalized polymers typically contain less than about 20 mer units, and more typically less than about 10 mer units, and thus have a typical maximum molecular weight less than about 3000, and more typically less than about 1000. Typically, these polymers comprise at least two mer units and more typically at least about 4 mer units and thus have a typical minimum molecular weight of at least about 250, and more typically of at least about 500. Obviously, the exact molecular weight of these polymers, especially the polymers of few mer units, is significantly dependent upon the molecular weight of the hydrophobe. Also obviously, the molecular weight of these polymers, and the nonfunctionalized polymers as well, is impacted by the definitions of $R_1-R_5$ and x. Thus where $R_1-R_5$ are the larger members (based in molecular weight) of their respective classes, the 3000 typical maximum molecular weight for functionalized polymers may be exceeded.

The polyhalide anions here used are of the formula $(XY_{2n})^-$ where the substituents are as previously defined. Typical polyhalide anions include $Br_3^-$, $Br_5^-$, $Br_7^-$, $I_3^-$, $I_5^-$, $I_7^-$, $BrI_2^-$, $ClI_2^-$, $IBr_2^-$, $ClBr_2^-$, $BrCl_2^-$, $ClBr_4^-$, $ICl_2^-$, etc. Although not included in the formula $(XY_{2n})^-$, $IBrCl^-$ is also a polyhalide of this invention. As noted in Schoenbeck, U.S. Pat. No. 3,101,250, the polychloride anions are unstable at ambient temperature unless maintained in an atmosphere of chlorine. Dissociation of flourine containing polyhalides is also too high for practical use at room temperature. The polyhalide anions of either or both bromine and iodine are preferred, with the polyhalide anions of iodine especially preferred.

The cations here used are selected from the group consisting of alkali metals, alkaline earth metals, hydrogen and mixtures thereof. Typical cations include hydrogen, sodium, potassium, lithium, magnesium and calcium. Preferred cations are sodium, potassium and hydrogen, with hydrogen being most preferred.

It is a characteristic of this invention that the cations are not taken from the polymer. In prior art compositions, as halogen is organically bound, hydrogen cations can become available. The cations of the present invention are independently supplied from sources external to polymer, that is they are added to the composition.

The most typical source of the cations is a halide salt which is added to convert a halogen into a polyhalide. For example, KI is added to $I_2$ to form $KI_3$. The potassium cation comes from a source external to the polymer. It is understood that the cation may be incorporated into the composition in numerous ways, and such ways are contemplated by the invention as long as the cations have a source external to the polymer.

The cation is present in an amount of at least 10 percent of the stoichiometric equivalent of the polyhalide anion. Preferably the cation will be present in an amount of at least 90 percent of the stoichiometric equivalent of the polyhalide anion. Most preferably the cation will be present in an amount equal to the stoichiometric equivalent of the polyhalide anion, although a stoichiometric excess of the cation is feasible and is contemplated by the subject invention.

The complexes of this invention are readily prepared at room temperature in either an aqueous or anhydrous state. The aqueous complex is made by a method comprising contacting a polymer comprising a plurality of ring-opened units of a 2-oxazoline or 2-oxazine monomer corresponding to the formula

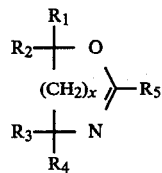

(III)

where $R_1-R_5$ and x are as defined above; $IBrCl^-$ or a polyhalide anion of the formula $(XY_{2n})^-$ where X, Y and n are as defined above; an independently supplied cation selected from the group consisting of alkali metals, alkaline earth metals, hydrogen and mixtures thereof; and water. A specific example of an aqueous preparation included contacting an aqueous solution or slurry of a poly-2-oxazoline or poly-2-oxazine with an aqueous solution of iodine and an alkali metal or alkaline earth metal iodide or HI. The resulting aqueous complex can then be recovered as a solid by simply subjecting the aqueous complex to drying.

A typical anhydrous preparation involves mixing an aqueous solution of a poly-2-oxazoline or poly-2-oxazine with an alkali metal iodide, drying the resulting mixture and subsequently grinding it to a relatively fine powder. The dried, ground polymer-iodide mixture is then blended with solid iodine at a suitable ratio, the blending accomplished by any convenient means, such as milling, rolling, etc. The procedure described in U.S. Pat. No. 3,898,326 for preparing polyvinylpyrrolidone-polyiodide solid complexes is usable for preparing the polymer-polyhalide solid complexes of this invention.

The composition of the complexes of this invention can vary considerably. Typically, the polymer:polyhalide anion weight ratio ranges from about 99:1 to about 35:65 and, preferably from about 85:15 to about 50:50.

Polyhalide anions are formed from the combination of a halide anion, such as chloride, bromide or iodide, with either a halogen or an interhalogen, such as chlorine, bromine, iodine, bromine chloride (BrCl), iodine chloride (ICl), iodine bromide (IBr), iodine trichloride ($ICl_3$), etc. As such, the complexes of this invention contain some amounts of all three entities, i.e. polyhalide anion, halogen, and halide anion. The polyhalide anion is present in the complex when the halogen or interhalogen:halide ratio is less than about 1:0.1, and preferably less than about 1:0.4. The typical minimum ratio is about 1:2 and, generally 1:1. Such amounts of halogen or interhalogen and halide maintain the presence of polyhalide anion in the complex.

Complexes of polyvinylpyrrolidone and polyhalide anion contain at least minor amounts of bound halide, i.e. halide chemically bound to the polymer. The bound halide in these polymers is lost halogen, i.e., halogen not available for sanitizing purposes, and is thought to be a result of uptake of the halide by the technical unsaturation of the polyvinylpyrrolidone. Since the polymers of 2-oxazoline and/or 2-oxazine have no such unsaturation, the amount of bound halide present in the instant complexes is essentially nil.

The solid complexes are usually colored solids which are soluble in polar solvents, such as water, methanol, tetrahydrofuran, isopropanol, etc. and essentially insoluble or only slightly soluble in relatively nonpolar solvents, such as methylene chloride, methyl cyanide, carbon tetrachloride, etc. The solid complexes are essentially odorless and their color varies, depending principally upon the type of halogen or interhalogen present. For example, a complex of poly(2-ethyl-2-oxazoline)/polyiodide anion is brown/black to amber/brown (depending upon particle size) while the same polymer complexed with polybromide is of an orange color. Like polymers complexed with $ICl_2^-$ or $BrCl_2^-$ are of a yellow color. This invention includes both the solid complexes and their various solutions. An aqueous solution of poly(2-ethyl-2-oxazoline)/polyiodide is of a reddish brown color while a solution of the same polymer complexed with polybromide, like the corresponding solid, is of an orange color. The solutions, like the solid complexes, are essentially odorless.

The complexes of this invention are used in the same manner as known halophor complexes. These complexes are useful as sanitizing agents due to their oxidative properties and thus find a multiplicity of uses in the medicinal and purification arts. Moreover, these complexes can be used in combination with other materials such as anionic and non-ionic detergents, or in combination with other halophors. The complexes of this invention can be used in a method for sanitizing or disinfecting a substrate contaminated with microorganisms by contacting the composition of the invention with the substrate. The contacting may be affected by dipping the substrate into the composition of the invention, but is preferably carried out by washing or scrubbing the substrate with the sanitizer or a formulation of the sanitizer with other materials such as detergents or other halophors. All conventional methods of contacting known to the art are encompassed by the scope of the invention.

One of the hallmarks of this invention is the high, total weight percent halogen that can be complexed with poly-2-oxazoline or poly-2-oxazine. Prior art complexes, particularly those of polyvinylpyrrolidone, do not provide the same degree of total weight percent halogen complex per unit of polymer. As such, the complexes of the instant invention permit the use of less polymer (the inert component of these complexes) for binding essentially the same amount of halogen. Moreover, compared to the complexes of polyvinylpyrrolidone, the instant complexes are highly soluble in water, their aqueous solutions are thus much less viscous on an equivalent percent solids basis, and thus the preparation of aqueous concentrates high in halogen content are more easily prepared. Such concentrates are desirable from a commercial perspective because they are easier to ship and store than their solid counterparts, avoiding such problems as dusting, etc. Further, more halogen is bound in available form by the complexes of this invention than those of the prior art. Still further, the instant complexes demonstrate relatively long shelf stability, little if any odor, little if any irritation to skin, and little if any corrosive effects. All this despite the fact that the complexes of this invention have a generally higher halogen content than the prior art complexes.

The following examples are illustrative of certain specific embodiments of this invention. Unless otherwise noted, all parts and percentages are by weight.

SPECIFIC EMBODIMENTS

The terms and tests here used are well-known in the art. "Distribution Coefficient (DC)" is defined and described in U.S. Pat. No. 3,028,300. "Starch Response Time (SRT)" is defined and described in U.S. Pat. No. 3,898,326. "Chloroform Test (CT)" is also defined and described in U.S. Pat. No. 3,898,326. Such terms as "total iodine (or halogen)", "Volhard iodine (or halogen)", etc. find definition in "Detergent/Iodine Systems", *Soap and Chemical Specialties*, (August, 1967) by Schmidt and Winicov. These terms are also widely used in the patent literature.

EXAMPLE 1

Aqueous Solution Complex Preparation

A stock solution of iodine and potassium iodide in water was prepared by mixing 40 parts iodine, 26 parts potassium iodide and 34 parts water. 17.5 Parts of this solution were then mixed with 82.5 parts of a 15.8 percent aqueous poly(2-ethyl-2-oxazoline) (PEOx) solution. The PEOx had a weight average molecular weight of about 100,000. The two solutions were mixed by stirring until a homogeneous solution of the two was formed (less than one hour). The resulting complex was determined to have a DC of 260 when 1 ml. of the 1.75 percent (as iodide) aqueous solution was extracted into 25 ml of n-heptane at 25° C.±1° C.

EXAMPLE 2

Aqueous complexes of PEOx/$I_3^-$ were prepared as in Example 1 where the PEOx:$I_2$ ratio was held at 90:10 and the halide varied. HI, KI and NaI were evaluated at an $I_2$:iodide weight ratio of 1:0.5. The resulting complexes were determined to have DC values of 364, 260 and 208 respectively, when 1 ml of a 1.75 percent (as iodine) aqueous solution was extracted into 25 ml of n-heptane at 25° C.±1° C.

EXAMPLE 3 AND CONTROL A

Anhydrous Complex Preparation

The solid complexes of both PEOx/iodine/iodide and polyvinylpyrrolidone (PVP)/iodine/iodide were prepared by the procedure outlined in U.S. Pat. No. 3,898,326. The PEOx had a weight average molecular weight of about 100,000 and the PVP had a K value of 30 and a number average molecular weight of about 40,000. A solution of the respective polymers and sodium iodide (NaI) (2 parts polymer:1.3 parts NaI was dried and subsequently ground in a Waring blender. The dried polymer was then sieved and the fraction that passed a 200 mesh screen was used for iodine complexing. The polymer-NaI composition was blended with iodine in ratios of 76.3:23.7, 69.2:30.8 and 61.7:38.3 by rolling on laboratory rolls for about 3 hours. After about 70 hours, the samples were subjected to a SRT. (A strip of moistened starch-iodide paper was held approximately 60 mm above the various complexes in a closed bottle. The time to develop any blue color on the paper was noted as the SRT.)

The complexes were also compared in a CT. The samples (0.5 g) of each complex were mixed with chloroform (5 ml) and shaken for 30 seconds. The mixture was then centrifuged and the color of the chloroform layer evaluated visually and by spectrophotometry at the iodine absorption peak (520 mμ).

The results of this example and control are reported in Table I. Also reported there are the manufacturing specifications for each sample and the initial titratable or available iodine determined by titrating with $Na_2S_2O_3$.

TABLE I

| ANHYDROUS POLYMER - IODIDE - IODINE COMPLEXES | | | | | | | |
|---|---|---|---|---|---|---|---|
| Parts by Weight | | | Manufacturing | Initial | | CT | |
| | (Provides) | | Pulv'd | Ratio | Titratable* | | | |
| PVP-Iodide | (PVP) | ($I^-$) | Iodine | Polymer:$I^-$:$I_2$ | Iodine (%) | SRT | Abs. | Color** |
| 76.3 | (48) | (23.7) | 23.7 | 2/1/1 | 23.2 | .4 min | 0.145 | 2 |
| 69.2 | (43.9) | (21.4) | 30.8 | 1.4/0.7/1 | 29.7 | 1 min | 0.585 | 3 |
| 61.7 | (39.2) | (19.1) | 38.3 | 1/0.5/1 | 37.9 | 10 sec | 1.95 | 4 |
| PEOx-Iodide | PEOx | $I^-$ | | | | | | |

TABLE I-continued

ANHYDROUS POLYMER - IODIDE - IODINE COMPLEXES

| PVP-Iodide | Parts by Weight (Provides) (PVP) | ($I^-$) | Pulv'd Iodine | Manufacturing Ratio Polymer:$I^-$:$I_2$ | Initial Titratable* Iodine (%) | SRT | CT Abs. | Color** |
|---|---|---|---|---|---|---|---|---|
| 76.3 | (48) | (23.7) | 23.7 | 2/1/1 | 24.6 | >20 min | 0.045 | 1 |
| 69.2 | (43.9) | (21.4) | 30.8 | 1.4/0.7/1 | 29.6 | 4 min | 0.11 | 2 |
| 61.7 | (39.2) | (19.1) | 38.3 | 1/0.5/1 | 37.8 | 45 sec | 0.69 | 3 |

*With 0.1 N $Na_2S_2O_3$
**Color Code
1 - Slight Pale Wine-Red
2 - Pale Wine-Red
3 - Wine-Red
4 - Deep Wine-Red The above data demonstrates several salient features of this invention. The SRT shows that less iodine escapes from the PEOx complexes than from the PVP complexes. This is generally indicative of greater shelf stability. The CT shows that the PEOx complexes extracted to a lesser degree than the PVP complexes at each iodine:iodide ratio as evidenced by less color imparted to the chloroform and consequently lower absorptions. Again, this is indicative that the PEOx complexes are more stable than the PVP complexes.

EXAMPLE 4

Aqueous PEOx-Bromine-Bromide Complex

Three solutions were prepared to demonstrate PEOx complexes with bromine and the effect of bromide (as potassium bromide) on the complex. Bromine was added to aqueous PEOx (weight average molecular weight of about 100,000) solutions (or aqueous PEOx and potassium bromide solutions when potassium bromide was included) and then placed on a mechanical shaker until dissolution occurred (generally after a few minutes). The solutions were then evaluated visually for bromine fumes. The results are reported in Table II.

In the solution where aqueous PEOx and bromine (no potassium bromide) was used, a portion (15 percent) of the bromine was converted to bromide (i.e., titratable with silver nitrate but not with sodium thiosulfate). The bromide was converted (about 5 percent) to a nontitratable species in all three solutions. The composition and results are also reported in Table II.

TABLE II

AQUEOUS PEOX-BROMINE-BROMIDE-COMPLEXES

| Solution | % Composition PEOx | $Br_2$ | KBr | % Analyzed $Br_2$* | $Br^{\ominus}$** | Observations |
|---|---|---|---|---|---|---|
| 1 | 18 | 2 | 1.48 (1% as $Br^-$) | 1.93 | 1.05 | No $Br_2$ fumes |
| 2 | 18 | 2 | 0 | 1.6 | 0.29 | Slight $Br_2$ fumes |
| 3 | 0 | 2 | 1.48 (1% as $Br^-$) | 1.92 | 0.98 | Heavy $Br_2$ fumes |

*Reacted with excess KI and titrated to a starch end point with $Na_2S_2O_5$.
**Reacted with excess $Na_2S_2O_5$ and titrated with 0.1N $AgNO_3$ via the Volhard method. Calculated as (% total $Br_2$ via Volhard) − (% $Br_2$ via $Na_2S_2O_3$) = % as $Br^-$.

Evidence of complexing is shown by the increased capacity of water to dissolve bromine when in the presence of PEOx. PEOx-bromine complexes without bromide are not shown because the bromide ion was spontaneously generated in solution 2.

EXAMPLE 5

(Spectrophotometric Analysis of PEOx-Iodine (Triiodide) Complexes)

Triiodide ($I_3^-$) has two characteristic absorption bands at approximately 290 mμ ($\epsilon_{max}$=45,000) and 365 mμ ($\epsilon_{max}$=25,000). These bands occur for uncomplexed triiodide and also for complexed triiodide. Several articles exist in the literature which describe typical absorption spectra for both triiodide and iodine complexes. See "Reaction of Polyamine Polymer with Molecular Iodine via Charge-Transfer Complex Formation", J. Polymer Science, 12, 167–181, (1074) by Tomono et al., for example. Polymer-iodine complexes absorb at higher wavelengths than polymer-triiodide complexes, the former typically in the 400–450 mμ region.

A PEOx/$I_3^{\ominus}K^{\oplus}$ complex (51/49 weight ratio) was prepared in water by mixing an aqueous PEOx solution (containing 25 percent PEOx) with an aqueous $KI_3$ solution (containing 25 percent $KI_3$). The complex was then diluted to provide an iodine ($I_2$) concentration of 0.019M. This solution was analyzed spectrophotometrically and was found to exhibit the characteristic triiodide bands at 365 mμ and 290 mμ with respective molar extinction coefficients ($\epsilon$) of 27,000 and 32,000.

EXAMPLE 6

Aqueous polymer:iodine:iodide complexes were prepared by mixing aqueous polymer solutions with the appropriate amount of Lugol's solution (5 g $I_2$, 10 g KI, 100 g $H_2O$) to obtain the desired ratios of polymer:$I_2$. The polymer plus $I_2$ concentration was 10 percent for each of the formulations although the actual percent solids (including the KI) varied from 11 percent for the 95:5 polymer:$I_2$ ratio to 17.1 percent for the 65:35 ratio. The actual percent solids was the same between directly compared PVP and PEOx samples.

TABLE III

| | BROOKFIELD VISCOSITY (cps at 25° C.) | |
|---|---|---|
| Polymer:$I_2$ Ratio | PEOx | PVP |
| 95:5 | 11 | 5 |
| 85:15 | 9 | 6 |
| 75:25 | 9 | 1150 |
| 65:35 | 16 | Semi-solid (Nonmeasurable) |

EXAMPLE 7

PEOx and PVP complexes were prepared in water at a 65:35 polymer:iodine ratio and 20 percent solids as polymer plus iodine. The compositions also contained KI in an Iodine:KI ratio of 1:0.7 for a total composition of 13 percent Polymer, 7 percent Iodine, 4.9 percent KI and 75 percent $H_2O$. The compositions were prepared by adding aqueous solutions of iodine and KI to stirred aqueous polymer solutions. The compositions were then allowed to mix on a mechanical shaker for several hours. The PEOx composition was a compatible, highly fluid dark red-brown solution. The PVP composition was a multiphase, noncompatible system containing a tarlike precipitate that resisted redissolving at more dilute concentrations in $H_2O$.

EXAMPLE 8

PEOx:triiodide and PVP:triiodide complexes having high iodine loadings were prepared in aqueous solutions. Iodine loadings of 10.7 and 16.0% using PEOx resulted in homogenous solutions having viscosities of 11,600 and 67,500 cps, respectively. Attempts to obtain 10.5 percent $I_2$ loading using PVP resulted in a coagulated multiphase system containing portions of uncomplexed $I_2$. Results are reported in Table IV.

TABLE IV

| Polymer Content | $I_2$ (%) | Polymers:$I_2$ | $I_2:I^-$ (ratio) | Solids (%) | Viscosity (cps, 72° F.) | Comments |
|---|---|---|---|---|---|---|
| 18.1% PEOx | 10.7 | 63:37 | 1:0.5 | 35.7 | 11,600 | |
| 27.2% PEOx | 16.0 | 63:37 | 1:0.5 | 53.7 | 67,500 | |
| 30.0% PVP | 10.5 | 75:25 | 1:0.5 | 47.0 | nonmeasurable | Multiphase contained non-complexed iodine. |

EXAMPLE 9

Using an 85:15 PEOx:$I_3^-$K$^+$ complex, a stock solution was prepared (in soft water) containing 1000 ppm iodine (active ingredient). The PEOx had a weight average molecular weight of approximately 100,000. 0.1 ml of E. coli. suspension was added to 9.9 ml of a test solution containing 10 ppm iodine. After 30 seconds, the samples were neutralized with thiosulfate solution, poured into Tryptone Glucose Extract Agar plates and allowed to solidify. Control cultures (American Type Culture Collection (ATCC) #11229) were also prepared which contained $9.75 \times 10^4$ cells/ml. The seeded plates were then incubated at 37° C. for 16–20 hours. Subsequent examination of the plates indicated that those treated with the polymer:triiodide complex (10 ppm $I_2$ level) exhibited no growth.

EXAMPLE 10

The procedure of Example 9 was repeated except that the test solution contained 200 ppm iodine and hard water was substituted for soft water. Subsequent examination of the plates indicated that those treated with the polymer:triiodide complex exhibited no growth.

EXAMPLE 11

Triiodide complexes were prepared as in Example 1 where the complexing agents were dodecylbenzene/-sulfonyl chloride initiated ethyloxazoline polymers containing 5, 7 and 10 ethyloxazoline (mer) units per initiating unit. The $I_2$:iodide weight ratio was 1:0.5 (present as KI). The complexes were determined to have DC values of 100, 116 and 161 for the 5 mer, 7 mer and 10 mer, respectively.

Both the PEOx and PVP polymers used in Examples 6–8 are of the same molecular weight as their respective counterparts in Examples 1–4.

Although this invention has been described in considerable detail through the above examples, such detail is for the purpose of illustration only, and should not be construed as a limitation upon the spirit of the invention or the scope of the appended claims.

What is claimed is:

1. A water-soluble solid complex comprising:
   (a) a polymer comprising a plurality of ring-opened units of a 2-oxazoline or 2-oxazine monomer corresponding to the formula

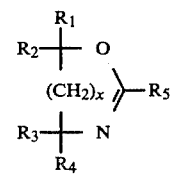

where $R_1-R_4$ are hydrogen or $C_1-C_3$ alkyl, $R_5$ is hydrogen or alkyl having up to about 18 carbon atoms, phenyl, or an inertly-substituted alkyl or phenyl, and x is 0 or 1;
   (b) IBrCl$^-$ or a polyhalide anion of the formula $(XY_{2n})^-$ where X and Y are individually chloride, bromide or iodide, but not both chloride, and n is 1, 2 or 3; and
   (c) a cation independently supplied from sources external to the polymer and selected from the group consisting of alkali metals, alkaline earth metals, hydrogen and mixtures thereof with the proviso that when the cation is hydrogen the ratio of halogen to halide in the complex is less than about 1:0.4.

2. The complex of claim 1 wherein $R_1-R_4$ are hydrogen, $R_5$ is a $C_1-C_4$ alkyl and x is 0.

3. The complex of claim 1 wherein (a) is poly(2-ethyl-2-oxazoline).

4. The complex of claim 1 wherein (c) is hydrogen, sodium or potassium.

5. The complex of claim 1 wherein (c) is hydrogen.

6. The complex of claim 1 wherein (c) is potassium.

7. The complex of claim 1 wherein said cation is present in an amount of at least 10 percent of the stoichiometric equivalent of the IBrCl$^-$ or the polyhalide anion.

8. The complex of claim 1 wherein said cation is present in an amount of at least 90 percent of the stoichiometric equivalent of the IBrCl$^-$ or the polyhalide anion.

9. The complex of claim 1 wherein said cation is present in an amount about stoichiometrically equivalent to, or greater than stoichiometrically equivalent to the IBrCl$^-$ or the polyhalide.

10. The complex of claim 1 wherein (b) is IBr$_2^-$.

11. The complex of claim 1 wherein (b) is $I_3^-$.

12. The complex of claim 1, 10 or 11 wherein (a) has a weight average molecular weight between about 20,000 and about 500,000.

13. An aqueous solution of the complex defined by claim 1, 10 or 11.

14. The complex of claim 1 wherein the polymerization of the polymer (a) is initiated by an organic compound which imparts detectable hydrophobic character to the resulting polymer.

15. The complex of claim 14 wherein (a) is prepared from the ring-opening polymerization of 2-oxazoline and/or 2-oxazine monomers initiated by at least one member selected frowm the group consisting of a sulfonyl halide of a $C_8-C_{40}$ hydrocarbon; an ester of an organic acid; a $C_8-C_{40}$ alkyl halide; or a diphenyl ether sulfonyl halide.

16. The complex of claim 1 wherein (a) is of the formula

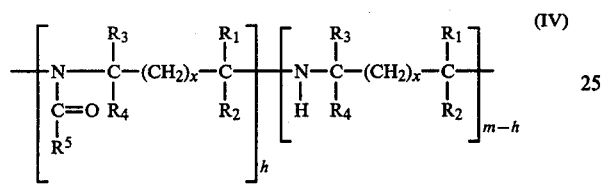

(IV)

where m is the total number of units, h is the number of acylated units, m-h is the number of deacylated units, and $R_1-R_5$ and x are as previously defined.

17. The complex of claim 16 wherein h is at least 50 percent of m.

18. The complex of claim 16 wherein h is at least 75 percent of m.

19. An aqueous complex made by a method comprising contacting:
(a) a polymer comprising a plurality of ring-opened units of a 2-oxazoline or 2-oxazine monomer corresponding to the formula

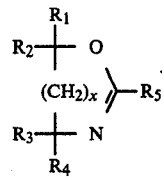

where $R_1-R_4$ are hydrogen or $C_1-C_3$ alkyl, $R_5$ is hydrogen or alkyl having up to about 18 carbon atoms, phenyl, or an inertly-substituted alkyl or phenyl, and x is 0 or 1;
(b) $IBrCl^-$ or a polyhalide anion of the formula $(XY_{2n})^-$ where X and Y are individually chloride, bromide or iodide, but not both chloride, and n is 1, 2 or 3;
(c) a cation independently supplied from sources external to the polymer and selected from the group consisting of alkali metals, alkaline earth metals, hydrogen and mixtures thereof with the proviso that when the cation is hydrogen the ratio of halogen to halide in the complex is less than about 1:0.4; and
(d) water.

20. The aqueous solution of claim 19 wherein the cation is contacted in the form of a halide salt.

21. A method for sanitizing or disinfecting a substrate contaminated with microorganisms comprising contacting said substrate with an aqueous solution of the complex of claims 1, 10, 11 or 19.

* * * * *

UNITED STATES PATENT AND TRADEMARK OFFICE
CERTIFICATE OF CORRECTION

PATENT NO. : 4,481,167
DATED : November 6, 1984
INVENTOR(S) : Sally P. Ginter and Percy J. Hamlin It is certified that error appears in the above—identified patent and that said Letters Patent is hereby corrected as shown below:

Title Page, Col. 2, line 4 under OTHER PUBLICATIONS, "196-" should read -- 196-218. --.

Title Page, Col. 2, line 4 under ABSTRACT, "or polyhalide" should read -- or a polyhalide --.

Col. 2, line 55, "Tomalia et.," should read -- Tomalia et al., --.

Col. 3, line 8, in the formula, "$R^5$" should read -- $R_5$ --.

Col. 6, line 1, "included" should read -- includes --.

Col. 8, line 14, "(as iodide)" should read -- (as iodine) --.

Col. 13, line 15, "frowm" should read -- from --.

Col. 13, line 28, in the formula, "$R^5$" should read -- $R_5$ --.

Signed and Sealed this

Twenty-third Day of April 1985

[SEAL]

Attest:

DONALD J. QUIGG

Attesting Officer    Acting Commissioner of Patents and Trademarks